United States Patent [19]

Jones

[11] Patent Number: 4,933,470
[45] Date of Patent: Jun. 12, 1990

[54] METHOD OF SYNTHESIS OF VICINAL DIAMINES

[75] Inventor: David S. Jones, Seattle, Wash.

[73] Assignee: NeoRx Corporation, Seattle, Wash.

[21] Appl. No.: 105,103

[22] Filed: Oct. 5, 1987

[51] Int. Cl.$^5$ ............................................ C07D 203/02
[52] U.S. Cl. .................................... 548/965; 564/511; 564/461; 564/487; 558/166; 558/145; 558/378
[58] Field of Search ....................... 564/511, 461, 487; 558/166, 145, 378; 548/965

[56] References Cited

FOREIGN PATENT DOCUMENTS 188256 7/1986 European Pat. Off. .

OTHER PUBLICATIONS

Harrison et al., Compendium of Organic Synthetic Methods, 1971, pp. 266–270.
Dermer et al., Ethlyenimine and Other Aziridines, 1969, pp. 206–222.
March, Advanced Organic Chemistry; Reactions, Mechanisms and Structures, 1968, p. 332.
Swift et al., Stereospecific Synthesis of cis and trans 1,2 Diaminocyclohexanes and Aliphatic Vicinal Diamines, J. of Org. Chem., 32(3) pp. 512–513.
D. S. Jones et al. "A Convenient Synthesis of Vicinal Diamines", Amer. Chem. SOc. Abstracts, 194th ACS National Meeting, New Orleans, Aug. 30-Sep. 4, 1987, Abstract No. 57.
G. Swift and D. Swern, "Stereospecific Syntheses of cis- and trans-1, 2-Diaminocyclohexanes and Alphatic Vicinal Diamines", The Journal of Organic Chemistry, vol. 32, No. 3, pp. 511–517, 1967.
H. Kohn and S.-H. Jung, "New Stereoselective Method for the Preparation of Vicinal Diamines from Olefins and Cyanamide", J. Am. Chem. Soc. 105: 4106–4108, 1983.
S.-H. Jung and H. Kohn, "Stereoselective Synthesis of Vicinal Diamines from Alkenes and Cyanamide", J. Am. Chem. Soc. 107: 2931-2943, 1985.
J. A. Deyrup, The Chemistry of Heterocyctic Compounds, vol. 42, "Small Ring Heterocycles", Part 1 (Aziridines et al.), A. Hassner, ed., Chapeter 1, John Wiley & Sons, N.Y., 1983.
W. E. Fristad et al., "Conversion of Alkenes to 1,2-Diazides and 1,2-Diamines", J. Org. Chem. 50: 3647–3649, 1985.
G. Swift and D. Swern, "Stereospecific Synthesis of erythro- and threo-9,10-Diaminooctadecanoic Acids and Derivatives", J. Organ. Chem. 31: 4226–4229, 1966.
Y. Ali and A. C. Richardson, "Nucleophilic Replacement Reactions of Sulphonate Esters. Part V. The Synthesis of Derivatives of 2,3,4,6-Tetra-amino-2,3,4-,6-tetradeosy-D-Glucose", J. Chem. Soc. (C), pp. 320–329, 1969.
G. Fraenkel and P. Pramanik, "Efficient One-Step Synthesis of a Cis Vicinal Tertiary Diamine and Its Complexation to a Lithium Carbanion Salt", J. Organ. Chem. 49: 1314–1316, 1984.
H. Natsugari et al., "Stereocontrolled Synthesis of Unsaturated Vicinal Diamines from Diels–Alder Adducts of Sulfur Dioxide Bis(imides)", J. Am. Chem. Soc. 106: 7867–7872, 1984.
R. Labia and C. Morin, "Unambiguous Preparation of a NaNβ Chemodifferentiated α,β-Diaminopropionic Ester Through Michael Addition onto a Dehydroalanine Derivative", J. Org. Chem. 51: 249–251, 1986.
C. D. Gutsche and G. C. Mei, "Association Phenomena. 7. Mixed Chelate and Comicellar Catalysis of Acetyl Phosphate 'Olysis' Reactions", J. Am. Chem. Soc. 107: 7964–7967, 1985.
L. H. DeRiemer et al., "Bledta II: Synthesis of a New Tumor-Visualizing Derivative of CO(III)-Bleomycin", Journal of Labelled Compounds and Radiopharmaceuticals, vol. XVIII, No. 10, pp. 1517–1534, 1980.
S. Kasina et al., "Tissue Distribution Properties of Technetium-99m-Diamide-Dimercaptide Complexes and Potential Use as Renal Radiopharmaceuticals", Journal of Medical Chemistry, vol. 29, No. 10, pp. 1933–1940, 1986.

Primary Examiner—Anton H. Sutto
Assistant Examiner—C. L. Cseh
Attorney, Agent, or Firm—Seed and Berry

[57] ABSTRACT

A method is described for producing vicinal diamines comprising the steps of converting a compound, possessing a leaving group on a carbon atom interposed between carbon atoms containing amino groups, to an aziridine-containing compound and reacting the latter compound with a nucleophile to form a vicinal diamine. The compound chosen for the rearrangement reaction may be selected from a wide range of compounds, including those with halide, heteroatom and aryl substituents. The amino groups may be blocked or unblocked. A variety of functional groups, including those which extend the carbon backbone, may be incorporated via opening of the aziridine-containing compound by addition of a selected nuclepohile. Aziridine-containing compositions and vicinal diamine compositions are disclosed. Functionalized vicinal diamines have numerous uses, including as intermediates for radionuclide-chelating ligands for use in the diagnosis and therapy of cancer.

12 Claims, No Drawings

1

METHOD OF SYNTHESIS OF VICINAL DIAMINES

TECHNICAL FIELD

The present invention is for a method of chemical synthesis of vicinal diamines and the compositions produced thereby.

BACKGROUND ART

Vicinal diamines are compounds which contain amino groups on adjoining positions on a carbon structure. The vicinal diamine group is commonly observed in naturally occurring compounds and plays an important role in medicinal chemistry, particularly in metal chelation. Despite the importance of this functional group, few general diamination methods exist. Furthermore, those methods that do exist are limited regarding their ability to include other functional groups on the molecule.

Vicinal diamines are most commonly prepared from olefins. Direct reaction of olefins with azide anion gives rise to vicinal diazides under electrochemical oxidation or transition metal oxidation with Mn(III), Fe(III), or Pb(IV). Alternatively, vicinal diazides can be prepared from epoxides via hydroxyazide intermediates or from vicinal dihalides via bimolecular nucleophilic substitution (referred to as "Sn2") reactions. The vicinal diazides can be reduced to amines; however, vicinal diazides are prone to many side reactions during reduction and require careful selection of reductants. Azides always present a possible explosion hazard as well.

There are less direct methods of preparing vicinal diamines from olefins. One such method converts olefins to iodocarbamates in a rather cumbersome manner involving iodoisocyanation and methanolysis of the isocyanate. Treatment of the iodocarbamate with hydroxide results in the formation of an aziridine which can be opened with ammonia to give vicinal diamines stereospecifically. Another method involves cycloaddition of chlorosulfonyl isocyanate to the olefin followed by a Curtius rearrangement and hydrolysis of the resulting cyclic urea. A third method involves the preparation of vicinal diamines from olefins and cyanamide/N-bromosuccinimide. A fourth method using olefins involves preparation from dienes via a Diels-Alder adduct of sulfur dioxide bis-imides.

Other methods of preparing vicinal diamines include reductive amination of an α-amino ketone, Michael addition of a urethane to a dehydroalanine derivative, reduction of α-amino nitriles which are prepared ultimately from aldehydes, and reduction of α-amino amides derived from amino acids.

In summary, the current methods of preparing vicinal diamines have a number of problems, including cumbersomeness, safety hazards, and limitations on how complex the product can be. Thus, there is a need in the art for a synthesis of vicinal diamines which is convenient, avoids azides, and allows for incorporation of a variety of functional groups. The present invention fulfills this need and further provides other related advantages.

DISCLOSURE OF THE INVENTION

Briefly stated, the present invention, in one aspect, provides compounds whose general structure possesses an amino group alpha to an aziridine ring. The amino nitrogen and the aziridine nitrogen may be unblocked or blocked. The compounds disclosed incorporate a wide range of functional groups on the general structure.

In another aspect, the invention provides vicinal diamine compounds. The amino groups may be blocked or unblocked. The compounds incorporate a wide variety of functional groups on the vicinal diamine backbone.

In yet another aspect, the present invention provides a method for preparing vicinal diamines. The method comprises: (a) converting a compound, possessing a leaving group on a carbon atom which is between carbon atoms containing amino groups, to an aziridine-containing compound; and (b) reacting the aziridine-containing compound with a nucleophile to form a vicinal diamine compound.

The compound chosen for the rearrangement reaction may be selected from a wide range of compounds, provided that a carbon atom containing a leaving group is interposed between carbon atoms each bonded to an amino group. In its most simple form, the compound is 1,3-diamino propane with a leaving group in the 2 position. The amino groups may be unblocked or blocked, depending upon which subsequent reactions are chosen.

The aziridine-containing compound is produced by formation of a bond between one of the amino groups and the carbon atom from which the leaving group has left. The conversion to the aziridine-containing compound may be accomplished in a variety of ways. The aziridine ring is opened by addition of a nucleophile to yield a vicinal diamine.

Other aspects of the invention will become evident upon reference to the following detailed description.

DETAILED DESCRIPTION OF THE PREFERRED EMBODIMENTS

In the present application, aziridine-containing compounds, vicinal diamine compounds, and a new method for the synthesis of vicinal diamines are disclosed. The synthesis is achieved by utilizing a rearrangement reaction that proceeds via an aziridine-containing compound. One advantage of this method is that the reaction takes place with the simultaneous incorporation of a wide range of functional groups. Additionally, the reaction will proceed in the presence of other functional groups on the precursor molecule. Functionalized vicinal diamines have numerous uses, including a intermediates for $^{99m}$Tc and $^{186}$Re/$^{188}$Re chelating ligands for use in the diagnosis and therapy of certain types of cancer.

Another advantage of the method disclosed is the directness of the synthesis route and the commercial availability of reactants. Starting with a diamine which contains a suitable leaving group interposed between the amino groups, the vicinal diamine is produced from only two steps. Further, a preferred precursor, 1,3-diamino-2-hydroxypropane, is commercially available.

Yet another advantage of the present invention is that it avoids the use of an azide or diazide. Thus, the possibility of an azide-induced explosion or side reaction during reduction is eliminated.

The method of synthesis is depicted by the following general formulae:

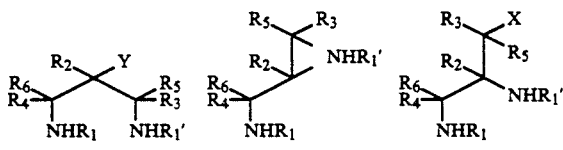

I  II  III

A compound of general formula I is converted to an aziridine-containing compound of general formula II. Compound I may be converted to compound II by a variety of methods, such as by the addition of base, acid, heat, radiation, or free radical initiator. Suitable bases include metal hydrides, alkoxides, hydroxide, amines, and metal cyanides in the presence of a crown ether, i.e., a macrocyclic polyether. Preferred bases are the metal hydrides, e.g., NaH, and the alkoxides, such as methoxide and t-butoxide. $R_1$ may be a hydrogen (H) or an amino-protecting group. Likewise, $R'_1$ may be a hydrogen (H) or an amino- protecting group. Preferred amino-protecting groups such as carbobenzyloxy (CBZ), t-butoxycarbonyl (t-BOC), and $SO_2C_6H_4CH_3$ (tosyl) yield carbamates (from CBZ or t-BOC) and sulfonamides (from tosyl). $R_2$, $R_3$, $R_4$, $R_5$ and $R_6$ may be independently selected from hydrogen (H), alkyl, acyl, aryl, halides, cyano, NRR', OR, SR, $SO_2R$, and $PO_3R$ groups, where R and R' are H, alkyl, acyl or aryl. Y is a leaving group. Preferred leaving groups are halogens, $OSO_2R$ and $OPO_3R$, where R is O, alkyl, acyl or aryl. Particularly preferred leaving groups are $OSO_2CH_3$ and $OSO_2C_6H_4CH_3$.

The aziridine-containing compound, represented by general formula II, is then reacted with a nucleophile X to form a vicinal diamine of general formula III. Preferred nucleophiles include halogens, such as Cl, Br, I and At; organometallics; azides; and NRR', OR and SR, where R and R' may be H, alkyl, acyl or aryl. Suitable organometallics include Grignard reagents; $\beta$-ketoesters; di-esters, such as malonates; and metal cyanides. Examples of X when attached to general formula III via an organometallic include $-(CH_2)_n-OR$, $-(CH_2)_n-NRR'$, and $-(CH_2)_n-SR$, where R and R' may be H, alkyl, acyl or aryl.

Formulae II and III contain asymmetric centers, i.e., carbon atoms attached to four different atoms or groups with the consequence that optically active three-dimensional isomers exist. Since this method of synthesizing vicinal diamines (III) and the aziridines (II) involves the generation of one or more asymmetric centers, it is possible to generate the asymmetric centers enantiospecifically by optical induction. This can be done by including appropriate chiral groups as $R_1$, $R_1'$, $R_2$, $R_3$, $R_4$, $R_5$ or $R_6$ or by starting with an optically active diamine.

In a preferred embodiment, 1,3-diamino-2-hydroxypropane is converted to a compound where both amines are protected and the hydroxyl is derivatized to yield a suitable leaving group. In a variety of ways, such as by the addition of base, N,N'-[blocking group]-1,3-diamino-2-[leaving group]-propane is converted to N,N'-[blocking group]-2-aminomethyl-aziridine. The aziridine ring is opened by addition of a nucleophile which is then incorporated at the 3 position of the resulting propane derivative. Therefore, addition of a desired group to the 3 position is achieved by selection of the appropriate nucleophile.

A variety of functional groups, including those nucleophiles listed above, may be incorporated as appendages on the 3 position of the resulting 1,2-diamino propane derivative. Additional carbon atoms may be introduced into the propane backbone by addition of an organometallic nucleophile, such as a Grignard reagent or a malonate, to the aziridine-containing compound. Sulfonamide aminoprotecting groups are preferred when a Grignard reagent or malonate is used. Thus, not only does the synthesis method convert 1,3-diamino propanes to vicinal diamines, but it also provides a way to increase the complexity of the resulting propane derivative.

Alternatively, additional carbon atoms may be introduced by beginning the synthesis with a diamino compound larger than propane. Finally, a combination of the two ways of introducing more carbon atoms may be used.

To summarize the examples which follow, Example I, part A, discloses the preparation of an N,N'-biscarbobenzyloxy-protected aziridine. Part B provides the details of nucleophilic reactions in which the aziridine ring is opened to yield derivatized vicinal diamines. The derivatives described are the acetoxy, alcohol, chloride, and nitrile. Example II, part A, discloses the preparation of an N,N'-bis-tosyl-protected aziridine. Part B provides the details of nucleophilic reactions in which the aziridine ring is opened by nucleophiles that form carbon-carbon bonds to yield vicinal diamines with extended carbon backbones. The nucleophiles described are a Grignard reagent and a malonate which yield a methyl and a pentanoic acid derivative, respectively. Example III, part A, discloses the preparation of an N,N'-bis-(carbo-t-butoxy)-protected aziridine. Part B provides the details of nucleophilic reactions in which the aziridine ring is opened by nitrogen and sulfur nucleophiles to yield derivatized vicinal diamines. The derivatives described are the amino, N-substituted amino, S-substituted thiol, and azido. Example IV discloses the preparation of a vinyl derivative of a starting compound used in the preparation of vicinal diamines via an aziridine-containing compound.

The following examples are offered by way of illustration and not by way of limitation.

EXAMPLES

Example I

A. Synthesis of N,N'-bis-carbobenzyloxy-2-aminomethyl aziridine

The starting material, 1,3-diamino-2-hydroxypropane, was converted to the N,N'-bis-carbobenzyloxy derivative (1a). The latter was converted to the 2-methanesulfonate derivative (2a). By the addition of NaH, to 2a, the aziridine (3a) was formed. The experimental protocols were as follows:

N,N'-bis-carbobenzyloxy-1,3-diamino-2-hydroxypropane, 1a. To a solution of 18 g (200 mmol) of 1,3-diamino-2-hydroxypropane in 50 mL of 1N NaOH at 0° C. was added 62.8 mL (75 g, 440 mmol) of benzylchloroformate. The mixture was stirred vigorously for 18 h, and the resulting solid material was collected by vacuum filtration. Crystallization from EtOAc/hexanes yielded 17.7 g of needles: mp 122°–123°, $^1$H NMR (CDCl$_3$) 3.27 (d of d, 4H), 3.78 (m, 1H), 5.12 (s, 4H), 5.49 (m, 2H), 7.37 (m, 10H), IR (KBr) 3325, 1685 cm$^{-1}$. Anal. Calc'd. for $C_{19}H_{22}N_2O_5$: C, 63.67; H, 6.19; N, 7.82. Found: C, 63.60, H 6 17; N, 7.84.

N,N'-bis-carbobenzyloxy-1,3-diaminopropyl-2-methanesulfonate, 2a. To a suspension of 21.0 g (58.5 mmol) of 1a and 12.2 mL (8.87 g, 87.7 mmol) of Et₃N in 292 mL CH₂Cl₁₂ at 0° C. was added 4.98 mL (7.37 g, 64.4 mmol) of methanesulfonyl chloride over a six-minute period. The mixture became a clear solution by the time addition was complete and stirring was continued for 1 h at 0° C. The mixture was washed in succession with chilled 150 mL portions of 5% HCl solution, H₂O, 10% Na₂CO₃ solution, saturated NaCl solution, dried (MgSO₄), filtered and concentrated under vacuum to give 16.9 g (66%) of white needles: mp 93°-94°; ¹H NMR (CDCl₃) 2.97 (s, 3H), 3.48 (d of d, 4H), 4.73 (d of d, 1H), 5.13 (s, 4H), 5.49 (m, 2H), 7.22 (s, 10H); IR (KBr) 3300, 1690, 1540 cm⁻¹.

N,N'-bis-carbobenzyloxy-2-aminomethyl-aziridine, 3a. To 30 mL of anhydrous DMF under N₂ atmosphere was added 600 mg of NaH (60% oil dispersion) (15 mmol). The mixture was cooled to 0° C., and a solution of 6.54 g (15 mmol) of 2 in 30 mL of anhydrous DMF was added over 5 minutes. The mixture was stirred for 30 minutes at 0° C., poured into 200 mL of cold water and shaken in a separatory funnel with 200 mL of EtOAc. The EtOAc layer was washed with a saturated NaCl solution, dried (MgSO₄), filtered, and concentrated under vacuum to give 6.0 g of a viscous oil. Purification by medium pressure chromatography on silica gel (40% EtOAc/hexanes) yielded 3.04 g (60%) of oil: ¹H NMR (CDCl₃) 2.10 (d J=3Hz, 1H), 2.36 (d J=6Hz, 1H), 2.65 (m, 1H), 3 14 (m, 1H), 3.62 (m, 1H), 5.09 (s, 2H), 7.33 (s, 10H). ¹³C NMR (75 MHz, CDCl₃) 30.2, 37.4, 42.6, 67.5, 68.9, 128.6, 128.7, 129.0, 129.1, 136.1, 136.8, 156.8, 163.2; mass spectrum (CI) m/z (intensity) 341 (6), 91 (100).

B. Nucleophilic Ring Opening Reactions With Aziridine 3a

The aziridine 3a was found to undergo typical nucleophilic ring opening reactions. For instance, treatment of compound 3a with refluxing acetic acid produced the acetoxy derivative, 5, which could be further converted to the 2,3-diamino-1-propanol derivative, 6. The preparation of 5 can be accomplished directly from 2a by deprotonating to produce the aziridine, adding acetic acid, and heating. The chloride, 7, and the nitrile, 4, were also prepared from 2a either with or without isolation of the aziridine. The experimental protocols were as follows:

O-Acetyl-N,N'-bis-carbobenzyloxy-2,3-diaminopropan-1-ol, 5. To a solution of 4.41 g (10 mmol) of 2a in 50 mL of anhydrous THF at 0° C. under N₂ atmosphere was added 1.74 g (15 mmol) of potassium t-butoxide. The mixture was stirred for 20 minutes at 0° C., and 50 mL of acetic acid was added. The flask was fitted with a reflux condenser, and the mixture was refluxed for 20 minutes. The solvents were removed via rotary evaporator, and the residue was partitioned between 100 mL of H₂O and 100 mL of EtOAc. The EtOAc layer was dried (MgSO₄), filtered and concentrated to yield 3.3 g of oily solid. Purification by silica gel chromatography (50% EtOAc/hexanes) followed by crystallization from hexanes/EtOAc yielded 892 mg (22%) of a white solid: mp 125-126; ¹H NMR (CDCl₃) 2.01 (s, 3H), 3.15-3.59 (m, 3H), 3.80-4.15 (m, 2H), 5.14 (s, 4H), 5.60-5.15 (brd m, 2H), 7.38 (s, 10H).

N,N'-bis-carbobenzyloxy-2,3-diaminopropan-1-ol, 6: Hydrolysis of 5. To a solution of 212 mg (1.53 mmol) of K₂CO₃ in 0.5 mL of H₂O and 6 mL of MeOH was added 212 mg (0.53 mmol) of 5a. The mixture was stirred for 1 hour at 20° C. and partitioned between 20 mL of H₂O and 2×10 mL of EtOAc. The EtOAc layers were combined, dried (MgSO₄), filtered, and concentrated to yield a viscous oil. Trituration with hexane/Et₂O gave a white powder which was collected by vacuum filtration to yield 116 mg (61%) of 6: mp 103°-105°; ¹H NMR (CDCl₃) 3.10-3.96 (m, 6H), 5.10 (,s 4H), 5.55 (m, 2H), 7.35 (s, 10H); mass spectrum (CI) m/z (intensity) 359 (19) 251 (100) Anal. Calcd. for C₁₉H₂₂N₂O₅: C, 63.67; H, 6.19; N, 7.82. Found: C, 63.61; H, 6.36; N, 7.92.

N,N'-bis-carbobenzyloxy-1,2-diamino-3-chloropropane, 7. To a suspension of 200 mg of a 60% oil dispersion of NaH (5 mmol) in 25 mL of DMF at 0° C. was added dropwise a solution of 2.18 g (5 mmol) of 2a in 25 mL of DMF. The mixture was stirred for 1 h, and 40 mL of 5% HCl solution was added. The mixture was extracted with 50 mL of Et₂O. The Et₂O layer was washed with saturated NaCl solution, dried (MgSO₄), filtered, and concentrated to give 1.33 g (79%) of white solid which was recrystallized from EtOH/H₂O: mp 118°-119°; ¹H NMR (CDCl₃) 3.35 (m, 2H), 3.57 (m, 2H), 4.00 (m, 1H), 5.05 (s, 4H), 5.38 (m, 1H), 5.68 (m, 1H), 7.30 (s, 10H). ¹³C NMR (CDCl₃) 42.9, 45.3, 53.0, 65.8, 67.6, 67.7 127.5, 128.0, 128.6, 129.0, 136.6, 156.6, 157.7; IR (KBr) 1680, 1535, 1260, 735, 690 cm⁻¹, mass spectrum (CI) m/z (intensity) 377 (45), 333 (99), 181 (100).

3,4-(bis-carbobenzyloxy)-diaminobutyronitrile, 4. A mixture of 6.55 g (15 mmol) of 2a, 1.08 g (16.5 mmol) of KCN, 0.40 g (1.5 mmol) of 18-crown-6 -ether, and 75 mL of anhydrous acetonitrile (stored over 3 angstrom molecular sieves) was refluxed in a nitrogen atmosphere for 19 h. When cool, the mixture was partitioned between 100 mL of 10% NaHCO₃ solution and 200 mL of CH₂Cl₂. The CH₂Cl₂ layer was washed successively with 100 mL portions of 5% HCl solution, H₂O and brine. The CH₂Cl₂ phase was dried (MgSO₄), filtered, and concentrated to give 5.47 g of brown oil. Two recrystallizations from CHCl₃/hexane yielded 2.68 g (40%) of 4 as a white solid: mp 111°-112°; ¹H NMR (CDCl₃) 2.65 (d J=6Hz, 2H), 3.42 (two overlapping doublets, 2H), 3.97 (m, 1H), 5.13 (s, 4H), 5.35 (brd s, 1H), 584 (brd s, 1H), 7.35 (s, 10H); mass spectrum (CI) m/z 368 (24), 325 (93), 181 (88), 107 (100).

EXAMPLE II

A. Synthesis of N,N'-bis-(p-toluenesulfonyl)-2-aminomethyl-aziridine

The starting material, 1,3-diamino-2-hydroxypropane, was converted to the tosylated derivative (2c). By the addition of NaOMe to 2c, the aziridine (3c) was formed. The experimental protocols were as follows:

N,N'-O-tris-(p-toluenesulfonyl)-1,3-diamino-2hydroxypropane, 2c. To a solution of 9.0 g (100 mmol) of 1,3-diamino-2-hydroxypropane in 200 mL of pyridine at 0° C. was added in portions 61.9 g (330 mmol) of p-toluene-sulfonyl chloride. The mixture was stirred at room temperature overnight and poured onto 200 g of crushed ice. After 1-2 h, the mixture formed a granular pink solid which was collected by filtration to give 48.4 g (87%) of crude 1c, which was used as is. An analytical sample was prepared by silica gel chromatography (50% EtOAc/hexanes) and concentrated under vacuum to give a white foam: ¹H NMR (CDCl₃) 2.49 (s, 9H0, 3.20 (d of d, 4H), 4.62 (t, 1H), 5.43 (t, 2H), 7.11–8.00 (m, 12H).

N,N'-bis-(p-toluenesulfonyl)-2-aminomethylaziridine, 3c. To a solution of 5.52 g (10 mmol) of 2c in 50 mL of MeOH at 0° C. was added dropwise over 2 minutes, 20 mL of 1 N NaOMe. The mixture was stirred for 1 h at 0° C. and partitioned between 125 mL of EtOAc and 2 x 125 mL of saturated NaCl. The EtOAc layer was dried (MgSO$_4$), filtered, and concentrated to yield an oil. The oil was purified by silica gel chromatography (40% EtOAc/hexanes), concentrated to an oil, and triturated with Et$_2$O to give 2.42 g (63%) of 3c as a white solid: mp 118°–119°; $^1$H NMR (CDCl$_3$) 2.22 (d J=4Hz, 1H), 2.44 (s, 3H), 2.49 (s, 3H), 2.55 (d J-7Hz, 1H), 2.91 (m, 1H), 3.06 (m, 1H), 3.18 (m, 1H), 4.98 (t, 1H), 7.31 (d J=8Hz, 2H), 7.36 (m J=8Hz, 2H),7.71 (d J=8Hz, 2H), 7.79 (d J=8Hz, 2H). $^{13}$C NMR (CDCl$_3$) 22.3 (q), 32.5 (t), 38.6 (d), 43.8 (t), 127.5 (d), 128.5 (d), 130.3 (d), 134.5 (s), 137.1 (s), 144.1 (s), 145.5 (s). Mass spectrum (CI) m/z (intensity) 381 (100), 155 (95). Anal. Calcd. for C$_{17}$H$_{20}$N$_2$O$_4$S$_2$: C, 53.66; H, 5.30; N, 7.36; S, 16.85. Found: C, 53.78; H, 5.39; N, 7.41; S, 16.73.

B. Nucleophilic Ring Opening Reactions With Aziridine 3c

Carbon-carbon bonds were formed by using Grignard reagents to open up the aziridine ring. For example, compound 3c could be converted to compound 8 by refluxing with methyl magnesium bromide in THF.

N,N'-bis-(p-toluenesulfonyl)-1,2-diaminobutane, 8: Addition of Methyl Magnesium Bromide to 3c. To a solution of 380 mg (1 mmol) of 3c in 5 mL of anhydrous THF under N$_2$ atmosphere was added 1 mL (3 mmol) of 3 M MeMgBr solution in diethyl ether, and the mixture was refluxed for 15 h. When cool, the mixture was partitioned between 20 mL of pH 7 buffer and 2×20 mL of EtOAc. The combined EtOAc layers were dried (MgSO$_4$), filtered, and concentrated to give 399 mg of oil which was purified by chromatography on silica gel (30% EtOAc/hexanes) to give an oil which solidified on trituration with Et$_2$O/hexanes. The solid was collected by vacuum filtration to give 116 mg of 8: $^1$H NMR (CDCl$_3$) 0.68 (t, 3H), 1.30 (m, 2H), 2.35 (s, 6H), 2.96 (m, 2H), 3.44 (m, 1H), 5.10 (m, 2H), 7.09–7.45 (m, 4H), 7.49–7.96 (m, 4H); mass spectrum (CI) m/z (intensity) 397 (100).

Alternatively, carbon-carbon bonds were formed by using the sodium salt of diethylmalonate to open up the aziridine ring, giving rise to compound 9 as a mixture of diastereoisomers. The crude mixture was hydrolyzed to the bis-tosylamide of 4,5-diaminopentanoic acid, 10, by refluxing in 6N HCl.

N,N'-bis-p-toluenesulfonyl-4,5-diamino-pentanoic acid, 10. To 380 mg (1 mmol) of 3c and 454 uL of diethyl malonate was added 10 mL of 0.3M NaOEt made by treating 100 uL of EtOH with 690 mg (330 mmol) of Na. The resulting solution was refluxed for 1.25 h and partitioned between 50 mL of H$_2$O and 50 mL of EtOAc. The EtOAc layer was washed with saturated NaCl, dried (MgSO$_4$), filtered, and concentrated to give 450 mg of viscous oil. To the oil was added 50 mL of 6N HCl, and the mixture was refluxed for 1.5 h. When cool, the mixture was extracted with 50 mL of EtOAc. The EtOAc layer was washed with saturated NaCl, dried (MgSO$_4$), filtered, and concentrated to give an oil which was crystallized from EtOAc/hexanes to give 208 mg (73%) of a white solid: mp 165°–166°; $^1$H NMR (CD$_3$OD) 2.08 (m, 2H), 2.70 (m, 2H), 3.26 (m, 2H) 3.65–4.25 (brd m, 1H), 7.34 (d J=8Hz, 4H), 7.60 (d J=8Hz, 2H), 7.70 (d J=8Hz, 2H); IR (KBr) 3660–2770, 1710, 1320, 1160, cm$^{-1}$; mass spectrum (CI) m/z (intensity) 423 (72), 269 (100). Anal. Calcd. for C$_{19}$H$_{24}$N$_2$O$_6$S$_2$: C, 51.70; H, 5.49; N, 6.36; S, 14.56. Found: C, 52.10; H, 5.62; N, 6.30; S, 14.33.

Example III

Synthesis of N,N'-bis-(carbo-t-butoxy)-2-aminomethylaziridine

The starting material, 1,3-diamino-2-hydroxypropane, was converted to the N,N'-bis-carbo-t-butoxy derivative (1b). The latter was converted to the 2-methane sulfonate derivative (2b). By the addition of NaH to 2b, the aziridine (3b) was formed. The experimental protocols were as follows:

N,N'-bis-carbo-t-butoxy-1,3-diamino-2-hydroxypropane, 1b. To a solution of 5.00 g (55.5 mmol) of 1,3-diamino-2-hydroxypropane in 140 mL of 1N NaOH and 50 mL of dioxane at 0° C. was added in portions 25.42 g (116.5 mmol) of di-t-butyl-dicarbonate. The mixture was allowed to come to room temperature and was stirred overnight. The mixture was partitioned between 100 mL of H$_2$O and 3 x 10 mL of CH$_2$Cl$_2$. The CH$_2$Cl$_2$ layers were combined and washed with 100 mL of H$_2$O followed by 100 mL of saturated NaCl solution. The CH$_2$Cl$_2$ later dried (MgSO$_4$), filtered, and concentrated to yield 17.63 g of viscous oil. Crystallization from Et$_2$O/hexanes yielded 13.74 g (85%) of 1b as a white solid: mp 98°–99.5°; $^1$H NMR (CDCl$_3$) 1.51 (s, 18H), 3.24 (d of d, 4H), 3.60–4.06 (brd m, 2H), 5.31 (brd m, 2H), IR (KBr) 3465, 3345, 3290, 1665, 1645, 1510, 1155 cm$^{-1}$.

N,N'-bis-carbo-t-butoxy-1,3-diaminopropyl-2-methanesulfonate, 2b. This compound was prepared from 1b in the same manner as described for the preparation f compound 2a to give a 96% yield of 2b as a white solid: mp 128–130 (dec); $^1$H NMR (CDCl$_3$) 1.42 (s, 18), 3.09 (s, 3H), 3.40 (d of d, 4H), 4.49–4.91 (m, 1H), 5.27 (brd m, 2H); IR (KBr) 3350, 1685, 1500, 1320, 1240, 1155, 900 cm$^{-1}$.

N,N'-bis-carbo-t-butoxy-2-aminomethyl-aziridine, 3b. To a suspension of 134 mg (5.43 mmol) of NaH (99%) in 18 mL of DMF under N2 atmosphere was added a solution of 2.00 g (5.43 mmol) of 2b in 5 mL of DMF. The mixture was stirred for 5 h at room temperature, diluted with 15 mL of H$_2$O, and extracted with 3×40 mL of EtOAc. The combined EtOAc layers were washed with a saturated NaCl solution, dried (MgSO$_4$), filtered, concentrated, and purified by silica gel chromatography (10% EtOAc/CH$_2$Cl$_2$) to give 1.40 g (95%) of 3b as an oil: $^1$H NMR (CDC13) 1.50 (s, 18H), 2.10 (d J-4Hz, 1H), 2.30 (d J=6Hz, 1H), 2.60 (brd m, 1H), 2.90–3.80 (m, 2H), 4.70–5.30 (s, 1H); mass spectrum (CI) m/z 273 (10), 217 (13), 189 (69), 117 (100).

B. Nucleophilic Ring Opening Reactions With Aziridine 3b

In addition to reactions with Grignard, malonate, halogen, and oxygen nucleophiles, the aziridine ring was opened up using sulfur, nitrogen and azido nucleophiles. Representative of the nitrogen nucleophiles were ammonia, which produced an aminopropane derivative (11), and N-methyl-2-aminoethanol, which produced an N-substituted aminopropane derivative (12). Representative of the sulfur nucleophiles was thiobenzoate, which produced an S-substituted mercaptopropane derivative (13). An azidopropane derivative (14) was prepared using hydrazoic acid. The experimental protocols were as follows:

2,3-di-(carbo-t-butoxyamino)-1-aminopropane, 11. Anhydrous ammonia was passed through a solution of 200 mg (0.73 mmol) of 3b in 5 mL of isopropyl alcohol for 30 minutes. The flask was stoppered and stirred at room temperature for 18 h. The solvent was removed, and the residue was purified by chromatography on silica gel (5% MeOH/0.5% Et$_3$N/CH$_2$Cl$_2$) to give 110 mg (55%) of recovered 3b and 70 mg (33%) of 10 as a yellow solid: $^1$H NMR: (CDC13) 1.55 (s, 18H), 2.80 (brd s, 2H), 2.90 (s, 2H), 3.35 (m, 2H), 4.75 (m, 1H), 5.20 (brd s, 1H), 5.50 (brd s, 1H); IR (neat) 3350, 2980, 2910, 1705, 1675 cm$^{-1}$; mass spectrum (CI) m/z 290 (12), 234 (12), 57 (100).

N-methyl-N-(2-hydroxyethyl)-2,3-di-(carbo-t-butoxyamino)-1-amino-propane, 12. To a solution of 220 mg (0.81 mmol) of 3b in 2 mL of CH$_3$CN was added 67 uL (61 mg, 0.81 mmol) of N-methyl-2-amino-ethanol. The mixture was refluxed for 12 h under N$_2$ atmosphere and concentrated under vacuum. Purification of the oily residue by silica gel chromatography (gradient: 2% MeOH/0.5% Et$_3$N/CH$_2$Cl$_2$ to 5% MeOH/1% Et$_3$N/CH$_2$Cl$_2$) gave 219 mg (58%) of 11 as an oily solid: $^1$H NMR (CDCl$_3$) 1.48 (s, 18H), 2.35 (s, 3H), 2.55 (d J=7Hz, 2H) 2.65 (m, 2H), 3.20–3.40 (m, 2H), 3.75 (5 J=7Hz, 2H), 3.80 (brd s, 1H), 5.38 (brd s, 2H).

S-benzoyl-2,3-di-(carbo-t-butoxyamino)-1-mercaptopropane, 13. To a solution of 131 mg (0.48 mmol) of 3b in 2 mL of THF as added 93 mg (0.53 mmol) of potassium thiobenzoate. An additional 2 mL of THF was used to rinse residual reagent into the reaction mixture, and the mixture was heated at 50° C. for 2.5 hours. When cool, the mixture was partitioned between 10 mL of EtOAc and 10 mL of H$_2$O. The EtOAc layer was washed with brine, dried (MgSO$_4$), filtered, and concentrated to give a white foam. Purification by silica gel chromatography (33% EtOAc/hexanes) yielded 34 mg (17%) of 12 as a white solid: $^1$H NMR (CDCl$_3$) 1.42 (s, 9H), 1.48 (s, 9H), 3.10–3.45 (m, 4H), 5.13 (brd, 2H), 7.19–7.64 (m, 3H), 7.85–8.14 (m, 2H).

2,3-di-(carbo-t-butoxyamino)-1-azidopropane, 14. To a solution of 1.64 g (6.00 mmol) of 3b in 15 mL of CHCl$_3$ was added 15 mL of a 2.0M solution of hydrazoic acid in CHCl$_3$. The mixture was stirred for 23 h and concentrated to a viscous oil. Purification by silica gel chromatography (20% EtOAc/hexane) gave 1.33 g (72%) of colorless oil which was crystallized from hexane to give 14 as a white solid: $^1$H NMR (CDCl$_3$) 1.38 (s, 18H), 3.06–3.97 (m, 5H), 5.00 (brd, 2H).

Example IV

Synthesis of N,N'-bis-carbo-t-butoxy)-1,3-diamino-2-vinyl-2-hydroxypropane (16)

The starting material, 1,3-diamino-2-hydroxypropane, was converted to the N,N'-bis-carbo-t-butoxy derivative (1b) according to the procedure described in EXAMPLE III(A). Compound (1b) was converted to the ketone (15) by oxidation with CrO$_3$ in pyridine.

To a suspension of 1.38 g (4.79 mmol) of 15 in 24 mL of THF at −78° was added dropwise over 10 minutes 15.8 mL of 1.0M vinyl magnesium bromide in THF. The mixture was stirred at −78° for 1 h and 0° for 1 h. To the 0° solution was added 30 mL of saturated (NH$_4$)$_2$SO$_4$ solution, and the mixture was extracted with 50 mL of H$_2$O. The ether layer was dried (MgSO$_4$), filtered, and concentrated to give a white solid. Recrystallization from hexane/EtOAc gave 937 mg (62%) of 16 as a white powder. An analytical sample was obtained by recrystallizing from hexane/CH$_2$Cl$_2$: MP 147°–148°; $^1$H NMR (CDCl$_3$) 1.32 (s, 18H) 3.07 (s, 2H) 3.19 (s, 2H), 3.72 (brd, 1H), 5.02 (brd, 2H) 5.02–6.04 (m, 3H); IR (nujol) 3465, 1700 cm$^{-1}$.

I claim:

1. A method for the synthesis of vicinal diamines, comprising the steps of:

converting by addition of base or heat, a compound of formula I to an aziridine-containing compound of formula II:

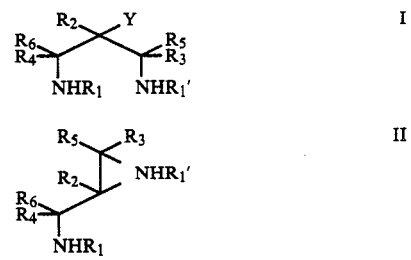

wherein R$_1$ is H or an amino-protecting group, R$_1$, is H or an amino-protecting group, Y is a leaving group, and R$_2$, R$_3$, R$_4$, R$_5$ and R$_6$ are independently selected from H, alkyl, acyl, aryl, cyano, NRR', OR, SR, SO$_2$R and PO$_3$RR' groups, where R and R' are H, alkyl, acyl or aryl; and reacting said aziridine-containing compound with a nucleophile X, wherein said nucleophile is selected from the group consisting of halogens, organometallics, azides, NRR', OR and SR, where R is H, alkyl, acyl or aryl and R' is H, alkyl, acyl or aryl, to form a vicinal diamine compound of formula III:

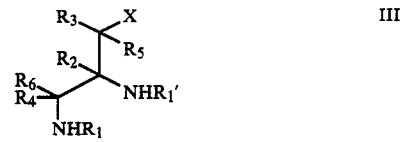

wherein R$_1$, R$_1$', R$_2$, R$_3$, R$_4$, R$_5$ and R$_6$ are as defined above.

2. The method of claim 1 wherein R$_1$ is an amino-protecting group which forms a carbamate or a sulfonamide from an amine and R$_1$' is an amino-protecting group which forms a carbamate or sulfonamide from an amine.

3. The method of claim 2 wherein the carbamate is formed by addition of a carbobenzyloxy or a t-butoxycarbonyl group.

4. The method of claim 2 wherein the sulfonamide is formed by addition of a tosyl group.

5. The method of claim 1 wherein the leaving group is selected from the group consisting of halogens, OSO$_2$R, and OPO$_3$R, where R is O, alkyl, acyl or aryl.

6. The method of claim 5 wherein the leaving group is OSO$_2$CH$_3$ or OSO$_2$C$_6$H$_4$CH$_3$.

7. The method of claim 1 wherein the organometallic is a Grignard reagent, β-ketoester, di-ester, or metal cyanide.

8. The method of claim 1 wherein the base is selected from the group consisting of metal hydrides, alkoxides, hydroxides, amines, and metal cyanide in the presence of crown ether.

9. The method of claim 8 wherein the metal hydride is NaH.

10. The method of claim 8 wherein the alkoxides are t-butoxide and methoxide.

11. The method of claim 1 wherein $R_2$, $R_3$, $R_4$, $R_5$ and $R_6$ are H.

12. The method of claim 1 wherein $R_1$, $R_1'$, $R_2$, $R_3$, $R_4$, $R_5$ or $R_6$ is a chiral group or attached to a chiral center.

* * * * *